(12) United States Patent
Bonsteel et al.

(10) Patent No.: US 9,588,034 B1
(45) Date of Patent: Mar. 7, 2017

(54) APPARATUS AND METHOD FOR AUTOMATED PERMEATION TESTING OF VAPOR AND LIQUID PENETRATION

(71) Applicant: U.S. Army Edgewood Chemical and Biological Command, APG, MD (US)

(72) Inventors: Russell A. Bonsteel, Providence, UT (US); Wesley D. Ercanbrack, Eagle Mountain, UT (US); Christopher A. Bailey, Lindon, UT (US); Kenneth D Nemelka, Alpine, UT (US); Nathan L. Porter, Kaysville, UT (US); Michael B. DeZearn, Abingdon, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 439 days.

(21) Appl. No.: 14/196,501

(22) Filed: Mar. 4, 2014

(51) Int. Cl.
*G01N 15/08* (2006.01)

(52) U.S. Cl.
CPC .......... *G01N 15/082* (2013.01); *G01N 15/08* (2013.01); *G01N 15/0806* (2013.01)

(58) Field of Classification Search
CPC .. G01N 15/08; G01N 15/0806; G01N 15/082; G01N 15/0826; G01N 2015/084; G01N 2015/086; G01N 15/00; G01N 2035/00346; G01N 2035/00356; G01N 2035/00376; G01N 35/10; G01N 33/346; G01N 33/367; G01F 1/42
See application file for complete search history.

(56) References Cited

U.S. PATENT DOCUMENTS

| | | | | |
|---|---|---|---|---|
| 2002/0004029 A1* | 1/2002 | Jang | ...................... | B82Y 30/00 423/613 |
| 2002/0168293 A1* | 11/2002 | Smith | .................. | G01N 33/367 422/68.1 |
| 2003/0074954 A1* | 4/2003 | Engle | ................. | G01N 15/0826 73/38 |
| 2014/0102177 A1* | 4/2014 | Kang | ..................... | G01N 13/00 73/38 |

* cited by examiner

*Primary Examiner* — Paul West
(74) *Attorney, Agent, or Firm* — Ulysses John Biffoni

(57) ABSTRACT

An apparatus and method for performing permeation testing on materials used in personal protective equipment is described. Two or more test cells are loaded with swatches of material and inserted into the testing apparatus. Chemicals to be tested on the material are loaded into one or more syringes and may be introduced into the top of the test cells as a liquid or a vapor. Vapor is collected from the bottom of the test cells, underneath the swatches of material, and tested for concentration of the chemicals being tested. The apparatus and method facilitates instantaneous breakthrough analysis, control of the sample environment and ease of operator use and calibration.

15 Claims, 16 Drawing Sheets

| Duration (min) | Split Flow (mL/min) | Pump Flow (µL/min) | Concentration (µg/cm$^2$/min) |
| --- | --- | --- | --- |
| 5 | 250 | 0.1 | 0.6 |
| 10 | 125 | 0.1 | 1.2 |
| 5 | 62 | 0.1 | 2.5 |
| 5 | 24 | 0.1 | 6.1 |
| 5 | 11 | 0.1 | 12.2 |
| 5 | 5 | 0.3 | 67.7 |
| 5 | 5 | 0.5 | 112.9 |
| 5 | 5 | 1.1 | 248.1 |
| 5 | 5 | 1.6 | 361 |
| 5 | 5 | 2.7 | 609.4 |
| 5 | 5 | 5.0 | 1128.6 |

FIG. 21

APPARATUS AND METHOD FOR AUTOMATED PERMEATION TESTING OF VAPOR AND LIQUID PENETRATION

STATEMENT OF GOVERNMENT RIGHTS

The invention described herein may be manufactured, used, and/or licensed by or for the Government of the United States of America.

BACKGROUND

The invention relates generally to materials testing and more particularly to evaluating materials used in personal protective equipment.

Personal protective equipment is used to protect workers involved in the production, use and transportation of toxic and hazardous chemicals. It is also used by military personnel and those involved in cleaning up after a dispersion of toxic and hazardous chemicals, accidental or otherwise.

Certification testing is often performed according to standards set by ASTM International (American Society for Testing and Materials) and NFPA (National Fire Protection Association). This testing requires evaluating the materials used in personal protective equipment and determines the level of protection provided in various situations. Of particular interest is the permeability of the material. Permeation refers to the penetration of a chemical, whether in liquid, gas or vapor form, through a solid. It is related to the concentration of the chemical and properties of the material. Certification tests are also referred to as permeation challenges.

The current methods of conducting permeation challenges are often slow and inconsistent. The methods rely on gathering instantaneous breakthrough data on permeation by manually reading the results of individual analyzers for the number of test cells being tested. The results of these readings must then be manually entered into a computer for analysis, a slow process which limits the number of samples that can be run by an individual in a day. Additionally, the current process does not insure that each test cell experiences identical conditions due to the cell placement in the laboratory hood. Different areas in the hood may experience very different temperatures or other conditions.

Thus, a need exists for a system that can automatically generate liquid and vapor permeation challenge results that are statistically valid and repeatable. There is also a need for a system that provides cumulative, as well as instantaneous breakthrough analysis, control of the sample environment and ease of operator use and calibration.

SUMMARY

An apparatus and method for performing permeation testing on materials used in personal protective equipment is described. Two or more test cells are loaded with swatches of material and inserted into the testing apparatus. Chemicals to be tested on the material are loaded into one or more syringes and may be introduced into the top of the test cells as a liquid or a vapor. Vapor is collected from the bottom of the test cells, underneath the swatches of material, and tested for concentration of the chemicals being tested.

DESCRIPTION OF THE DRAWINGS

Features of example implementations of the invention will become apparent from the description, the claims, and the accompanying drawings in which:

FIG. 21 depicts a table used to calculate flow rates for calibrating the apparatus.

DETAILED DESCRIPTION

If used and unless otherwise stated, the terms "upper," "lower," "front." "back," "over," "under," and similar such terms are not to be construed as limiting the invention to a particular orientation. Instead, these terms are used only on a relative basis. In addition, one of ordinary skill in the art would readily understand that various connections and ports described below are not limited to the specific locations depicted.

The present invention is an apparatus and method for testing swatches of material used in personal protective equipment. Swatches are loaded into test cells and subjected to either liquid challenge or vapor challenge tests. Operation of the apparatus and analysis of the results is performed with a computing device attached to the apparatus over a local area network.

Apparatus Description

Figure 1:
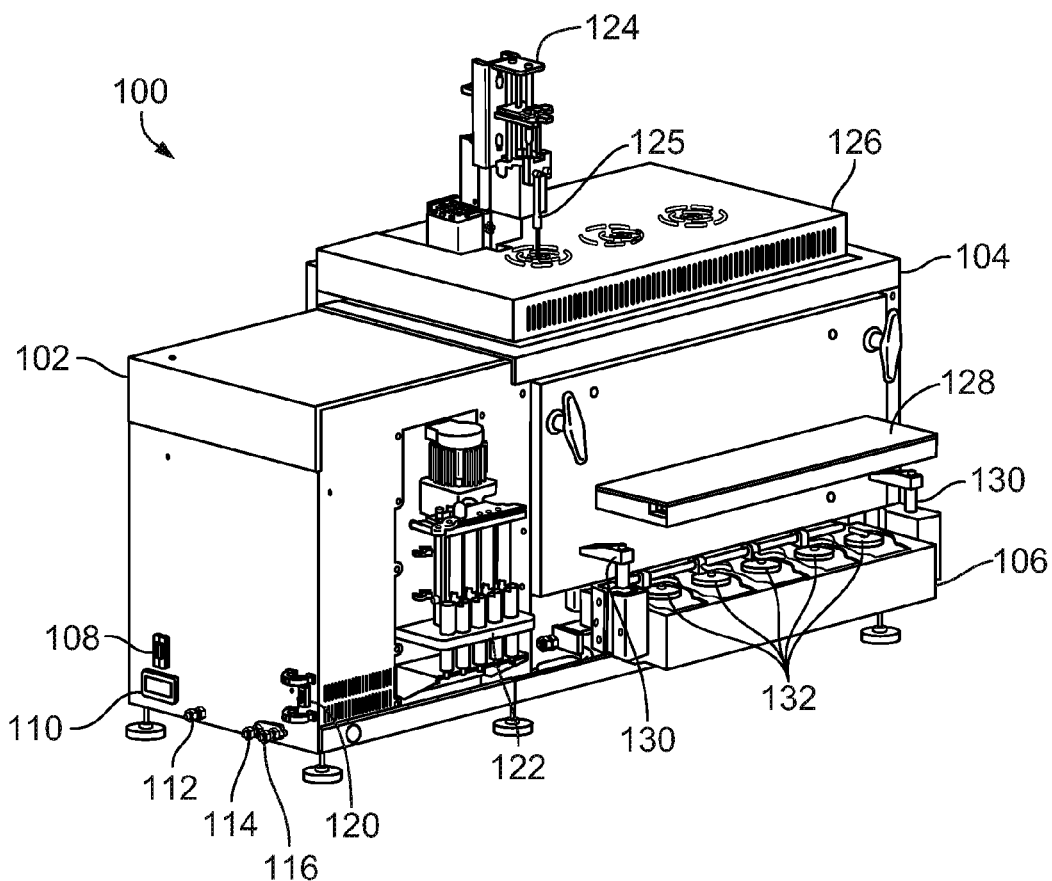
FIG. 1 is a diagram illustrating an overview of a permeation testing apparatus.

Turning to FIG. 1, a permeation testing apparatus 100 in one example comprises three main sections: electronics cabinet 102, oven 104 and swatch block 106. In a preferred embodiment, apparatus 100 is designed to fit inside a standard size hood and has dimensions of 25 inches deep, 48 inches wide and 29 inches high. These dimensions include all connections and peripheral devices. One of ordinary skill in the art would understand that the invention is not limited to these dimensions and that other design criteria could be chosen.

Electronics cabinet 102 includes assorted components which are used to control the operation of apparatus 100. These components are accessed by means of several ports, shown on the left side of cabinet 102. These ports include LAN (local area network) connection 108, power inlet 110 and power switch 120. Cabinet 102 also includes port 112 for air, port 114 for hydrogen and port 116 for helium. In a preferred embodiment, port 112 uses a inch fitting and is attached to a source of clean dry air maintained at a minimum pressure of 50 psi, port 114 uses a ⅛ inch fitting attached to a source of high purity hydrogen with a minimum pressure of 30 psi and port 116 uses a ⅛ inch fitting attached to a source of high purity helium regulated to 10 psi.

Figure 2:
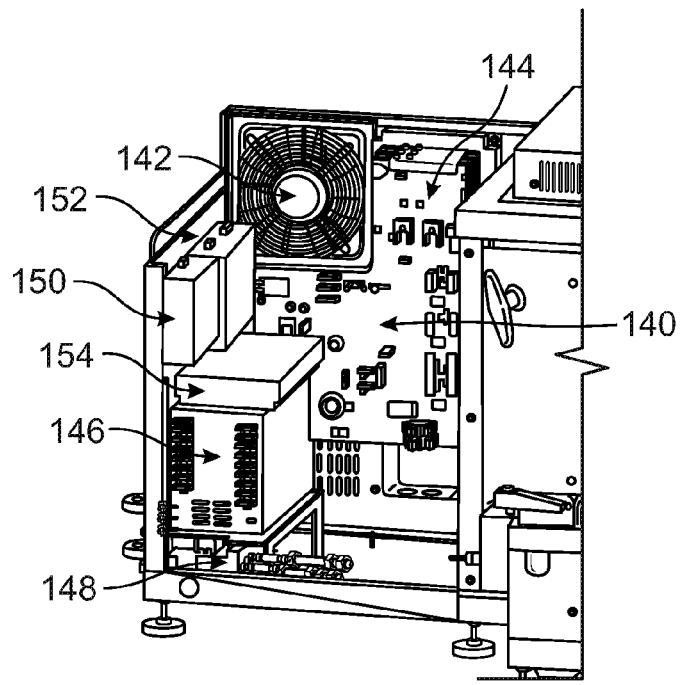
FIG. 2 illustrates components of an electronics cabinet for a permeation testing apparatus.

The inside of electronics cabinet 102 is shown in more detail in FIG. 2. The back of electronics cabinet 102 comprises a main board 140 for providing electrical and support connections for other components. All connections for electronic components in apparatus 100 are accessible from the front of apparatus 100. Other components in cabinet 102 include cabinet fan 142 for cooling cabinet 102 and connections 144 for a plurality of expansion boards. The expansion boards can be connected to other analyzer devices as required. Cabinet 102 also includes power supply 146, for example, a 24 V DC power supply, a gas inlet manifold 148 coupled to ports 112, 114 and 116 from FIG. 1, an injection valve controller 150 and a stream select valve controller 152. Cabinet 102 further includes a FID (flame ionization detector) electrometer 154. Optionally, the permeation tester can use a flame photometric detector either in addition to or instead of the FID.

Figure 3A:
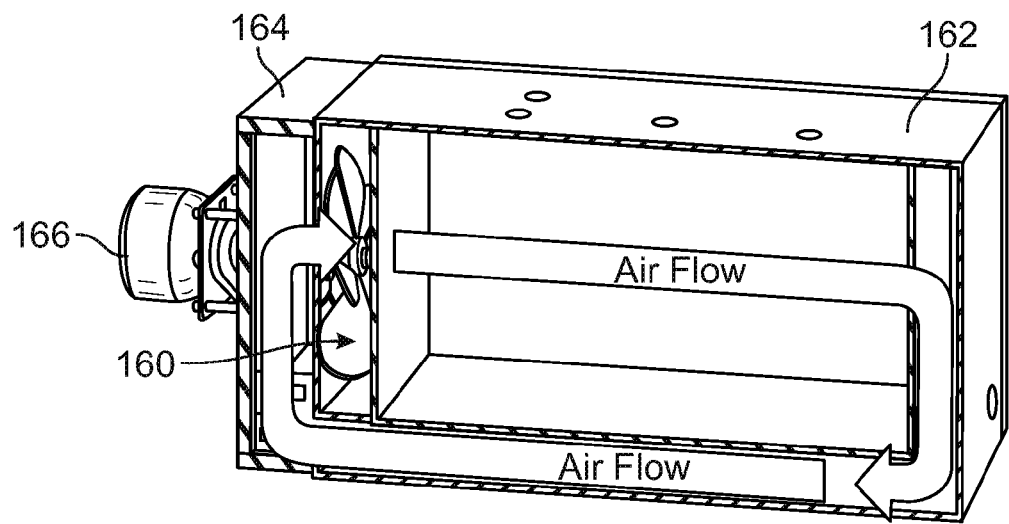
FIGS. 3A and 3B are diagrams illustrating components of an oven for a permeation testing apparatus.

The second component of FIG. 1, oven 104, is shown in more detail in FIG. 3A. Fan blades 160 generate a recirculating air flow through main compartment 162, under the bottom of the oven, then through heater manifold 164 as shown by the air flow arrows in the figure. Fan blade 160 is powered by motor 166. In a preferred embodiment, motor 166 and manifold 164 extend into electronics cabinet 102 of FIG. 1 and are removable for maintenance. Heater manifold 164 if depicted in more detail in FIG. 3B. Air flow from the oven passes over two heater elements 168 before being recirculated by fan blade 160. Thermostats 170 provide regulation of the temperature of the air flow. Heater elements 168 are individually powered from main board 140 in electronics cabinet 102 but are controlled so that both are on and off at the same time. Oven 104 helps to maintain the various testing components of apparatus 100 at a consistent temperature.

A top view of oven 104 will be described in connection with FIGS. 1 and 4. An analytical carrier gas injection port 124 is positioned on top of oven 104. Port 124 includes a mount for a syringe 125 of a chemical to be tested, and a pump for ejecting the contents of the syringe under control of components in electronics cabinet 102. Element 126 of FIG. 1 is a protective cover for several heating zones on top of the oven. Syringe 125 containing a chemical being used for a vapor challenge is loaded into port 124 and then injected through needle 180 into vaporizer 182 when performing a vapor challenge test. Carrier gas is injected through fitting 184. The contents of the syringe are injected into vaporizer 182 of FIG. 5 and combined with hydrogen or helium from ports 114 or 116 of FIG. 1. Referring back to FIG. 4, FID 186 is also positioned at the top of oven 104 and receives input of hydrogen and air through connections 188.

Figure 4:
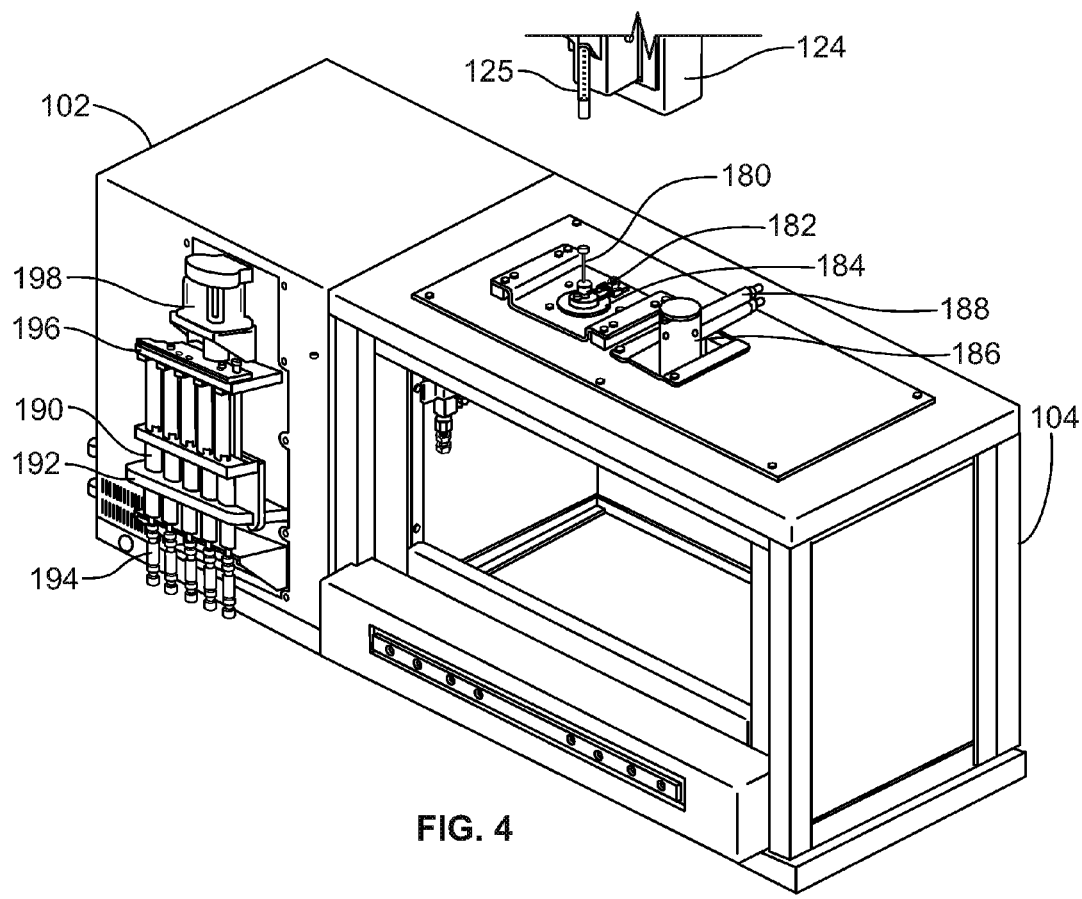
FIG. 4 illustrates the top of the oven of FIGS. 3A and 3B.

Still referring to FIGS. 1 and 4, a liquid challenge pump 122 mounted on the front of electronics cabinet 102 of FIG. 1 is shown in more detail in FIG. 4. Five syringes 190 holding toxic or hazardous chemicals to be tested are loaded into syringe holder 192. In a preferred embodiment, the syringes are SGE model 10MDR-LL-GT syringes but any appropriate model may be used. Luer check valves 194 provide a connection between syringes 190 and tubing leading to test cells 132 in swatch block 106, shown in FIG. 1.

A push plate 196 of FIG. 4 is controlled by motor 198 so that all syringes are emptied at an even consistent rate. Motor 198 is designed to deliver a 9.6 mL stroke each time is it activated. To introduce less than 9.6 mL of challenge chemical, fill syringe 190 with the appropriate amount of chemical then fill the remainder with air. In a preferred embodiment, syringes 190 are filled with no more than 8 mL of challenge chemical with 2 mL of air to push all chemical out of the sample lines and into the swatch test cell. In a further preferred embodiment, the delivery speed of the challenge pump is set to deliver about 2.5 mL per minute during an analytical run. Tubing length and diameter between syringes 190 and test cells 132 are set so that solvent will reach thermal equilibrium during delivery. In a preferred embodiment, tubing is FEP tubing with an ⅛" outer diameter, and a length of 82 cm.

Figure 5:
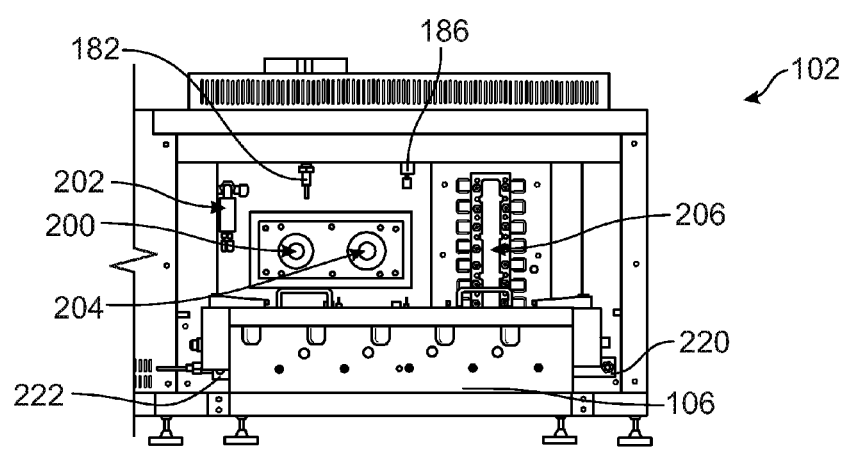
FIG. 5 illustrates the interior of the oven of FIGS. 3A and 3B.

Referring to FIG. 5, an interior view of oven 104 is shown. Vaporizer 182 is coupled to mixing tee 202 by a length of tubing (not shown to improve clarity of the figure). Mixing tee 202 ensures that the chemical being tested is evenly distributed throughout the vapor. When running a vapor challenge, an output of the mixing tee is connected to vapor challenge manifold 228 of FIG. 7 by connector 283, shown most clearly in FIG. 12. When performing a calibration operation, the output of the mixing tee is connected to a calibration flow port on stream selection valve 204. An injection valve 200, stream selection valve 204 and flow control vacuum manifold 206 are mounted in the back of the oven as shown in FIG. 5 with the electrical connections for these components are outside the oven and accessed using mounting plates which can be removed from inside the oven. Swatch block 106 is shown at the front of oven 102.

Permeation testing apparatus 100 of FIG. 1 also includes a vacuum attachment (not shown) on the right side of oven 104. Designing apparatus 100 to work with air drawn by a vacuum through the various flow paths improves safety since the vacuum system leaks will not result in chemical escaping from the apparatus. Instead air will be drawn into the leak. In a preferred embodiment, a vacuum pump is coupled to apparatus 100 via a Peltier electronically cooled outlet trip and a carbon trap as would be understood by one of ordinary skill in the art. After entering oven 104 by means of a inch Teflon line, the vacuum line is attached to flow control vacuum manifold 206 of FIG. 5 by connection 215 (shown in FIG. 6).

Figure 6A:
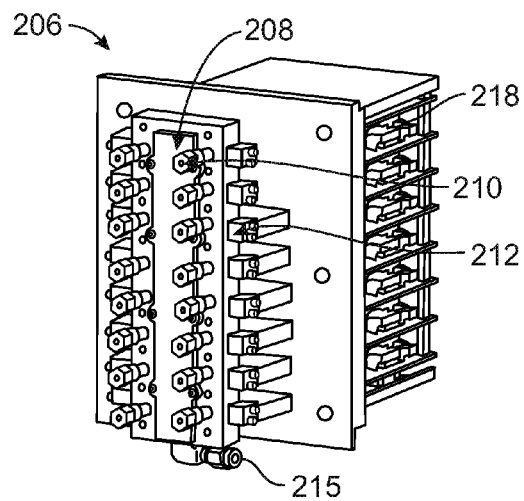
FIGS. 6A and 6B illustrate a flow control manifold for use in the permeation testing apparatus.
Figure 6B:
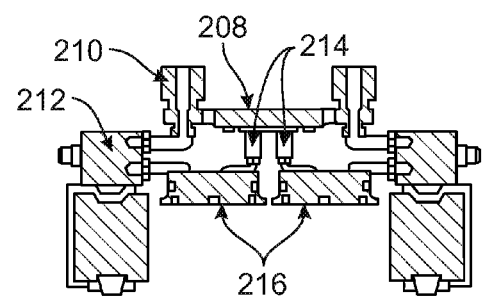

Flow control vacuum manifold 206 is shown in more detail in FIG. 6. It includes transducers 216, proportional control valves 212, fixed orifices 214 and electronic controls 218. The purpose of manifold 206 is to ensure that the flow of a gas or liquid is equally distributed among all test cells. The vacuum line is connected to the bottom of manifold 206 at connection 215. A vacuum chamber 208 extends through the length of manifold 206 with tube connection fittings 194 on either side of the vacuum chamber. Tube connection fittings 212 are provided for connection to swatch block 106 of FIG. 1 and other elements of apparatus 101 as will be explained below.

Referring to FIG. 1, a swatch block 106 is mounted to the front of oven 104. After challenge cells 132 are inserted in swatch block 106, lid 128 (depicted in a raised position in FIG. 1 so that inside of swatch block 106 is visible) is secured to swatch block 106 using hydraulic clamps 130. Clamps 130 are controlled through electronics cabinet 102 so as to mount lid 128 evenly to swatch block 106 and provide a secure, leak proof connection between test cells, connection lines in lid 128 and connections lines in swatch block 106.

Figure 7:
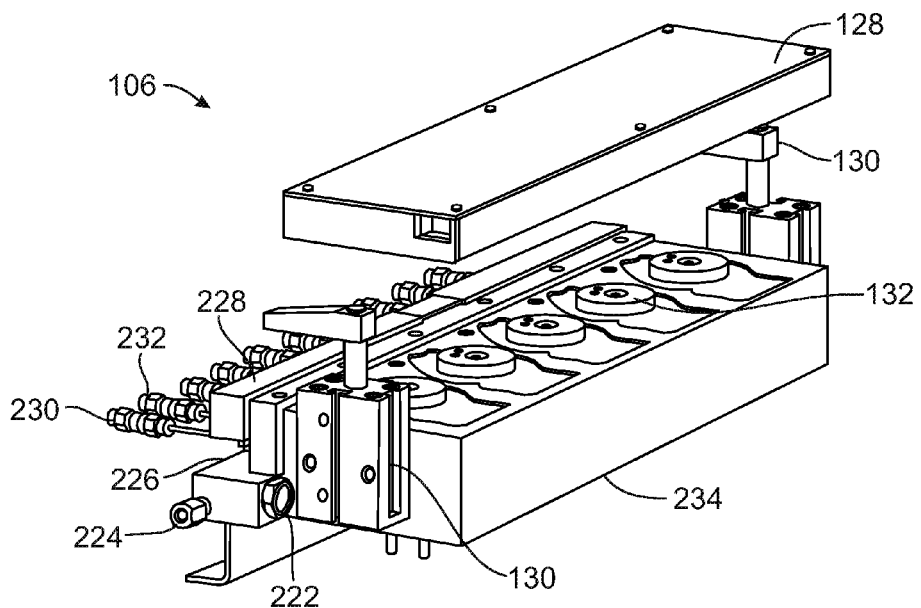
FIG. 7 illustrates a swatch block of the permeation testing apparatus.

Swatch block 106, removable lid 128 and hydraulic clamps 130 are shown in more detail in FIG. 7. In general, swatch block 106 includes an air distribution manifold 226, a chemical vapor challenge manifold 228 and a heater block 234. Heater block 234 includes openings for five test cells 132, described in more detail in FIGS. 9 and 10. As described above, permeation testing apparatus 100 is designed to work with air drawn by a vacuum through the test cells and other parts of the flow paths. An air inlet 220 at one end of swatch block 106 (and shown in FIG. 5) provides a source of air for the vacuum to draw into swatch block 106. An air outlet is shown at 224 which provides an exit for air inlet 220 on the opposite side of the swatch block through air distribution manifold 226. Connector 222 allows connection of a device to monitor the temperature and humidity of the air flow. Air flow into air inlet 220 may be left open or it can be connected to a source of humidified air. In a preferred embodiment, the connection for air inlet 220 is connected to ⅜ inch diameter tubing. Smaller tubing may cause a restriction point resulting in poor performance. The other end of the air manifold between air inlet 220 and air outlet 224 can either be vented directly into the hood since it is not in the chemical flow path. Alternatively air outlet 224 can be connected to a short ⅜ inch tube and directed to the back of the hood.

Swatch block 106 also includes a plurality of connectors 230 and 232 that provide a connection between test cells 132 and flow control manifold 206. They are described in more detail with reference to FIGS. 12 and 13.

Figure 8:
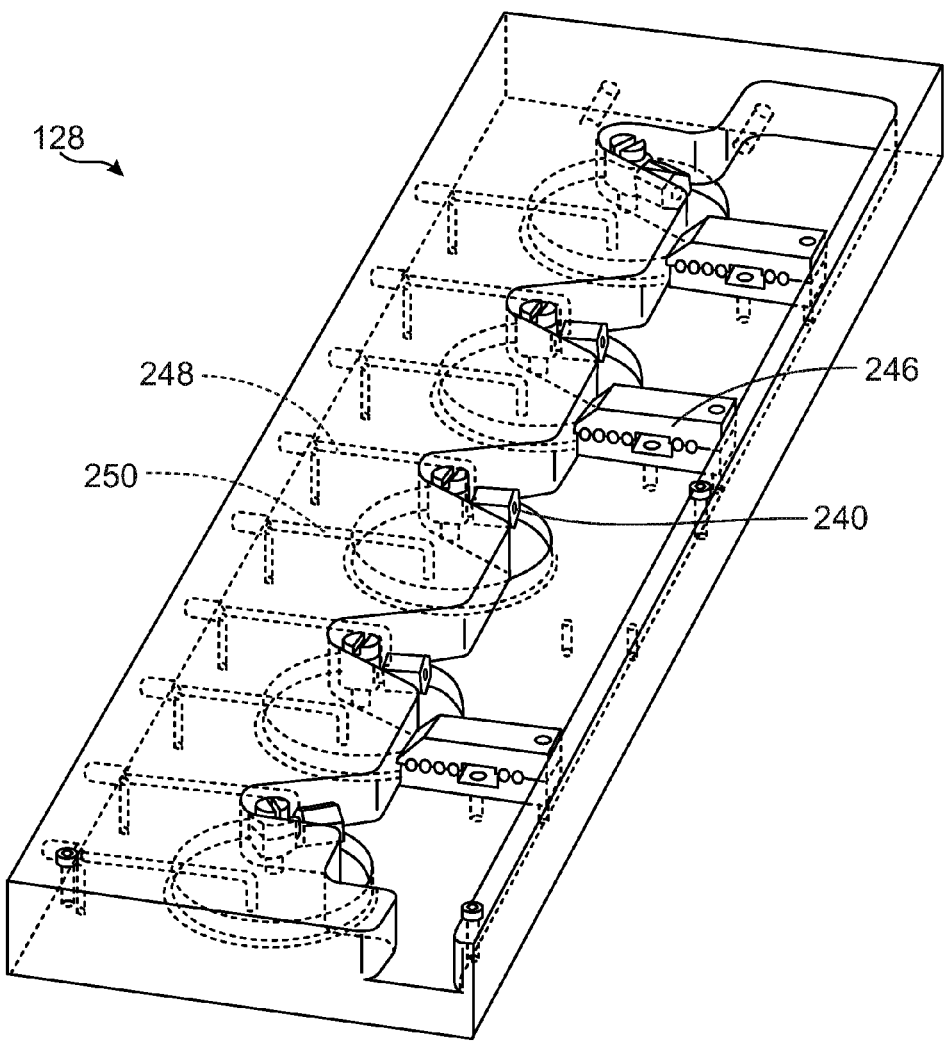
FIG. 8 illustrates a removable lid for the swatch block of FIG. 7.

FIG. 8 shows a more detailed view of removable lid 128. Liquid challenge port 240 is connected to tubing from the tubing connected to Luer locks 194 of FIG. 4. Although port 240 is only indicated for one test cell 132, each test cell is provided with an equivalent port as shown. Each test cell is also connected to a line 248, a vapor challenge outlet, and line 250, a vapor challenge inlet. These lines will be discussed in more detail with reference to FIGS. 12 and 13.

Figure 9:
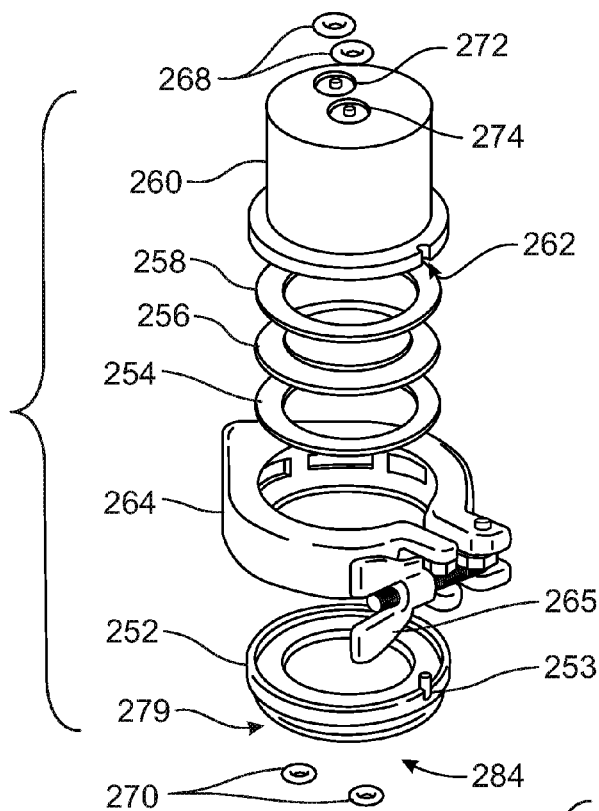
FIG. 9 illustrates a liquid challenge test cell for use with the swatch block of FIG. 7.

A liquid challenge cell is shown in FIG. 9. Cell bottom 252 includes an alignment pin 253. A first PTFE gasket 254 is placed in cell bottom 252, followed by swatch material 256 then a second PTFE gasket 258. For blank cells, aluminum foil is placed on top of the swatch before placing the second PTFE gasket 258 on the aluminum foil. Cell top/liquid reservoir 260 is placed on top of second gasket 258, making sure alignment notch 262 lines up with alignment pin 253 on cell bottom 252. Leak proof connection between the challenge cell and swatch block 106 and lid 128 is provided by O-rings 268 and 270. Cell clamp 264 slides around both the cell bottom and the cell top, and is tightened with wing nut 265. It is important that the alignment pin is between the open ends of the clamp and the wing nut is located to the left as depicted in FIG. 9 so that o-rings 268 and 270 will line up with the appropriate connections in swatch block 106 and lid 128. In a preferred embodiment, liquid challenge cells are made of stainless steel and clamp 264 is made of aluminum.

Figure 10:
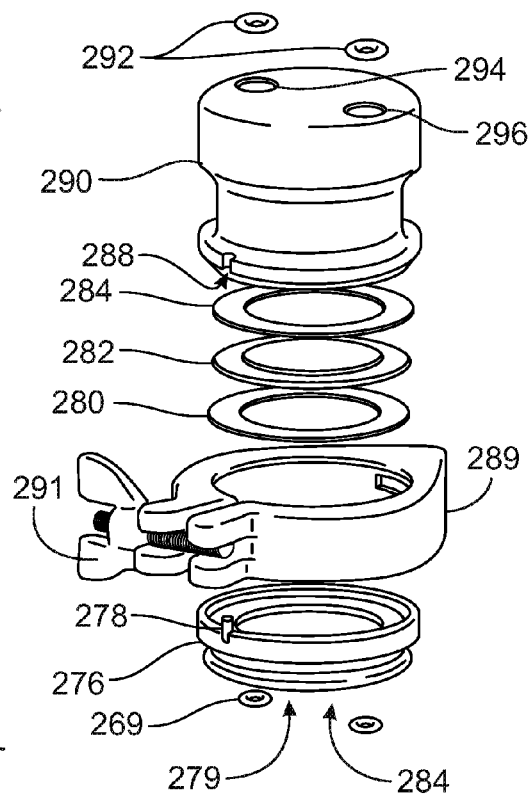
FIG. 10 illustrates a vapor challenge test cell for use with the swatch block of FIG. 7

A vapor challenge cell is shown in FIG. 10. Similarly to the liquid challenge cell of FIG. 9, the vapor challenge cell includes a cell bottom 276 with an alignment pin 278. Swatch material 282 is sandwiched between PTFE gaskets 280 and 284. For blank cells, aluminum foil is placed on top of swatch material 282. Cell top 290 is placed on top of the second gasket 284 such that alignment notch 288 lines up with alignment pin 278. Leak proof connection between the challenge cell and swatch block 106 and lid 128 is provided by O-rings 292 and 269. Cell clamp 289 slides around both the cell bottom and the cell top, and is tightened with wing nut 291. It is important that the alignment pin is between the open ends of the clamp and the wing nut is located to the left as depicted in FIG. 9 so that O-rings 292 and 269 will line up with the holes in swatch block 106 and lid 128. Connections 279 and 284 in the bottom of both the liquid and vapor challenge cells are used to test vapor as will be explained below. In a preferred embodiment, vapor challenge cells are made of stainless steel and clamp 289 is made of aluminum.

Figure 11B:
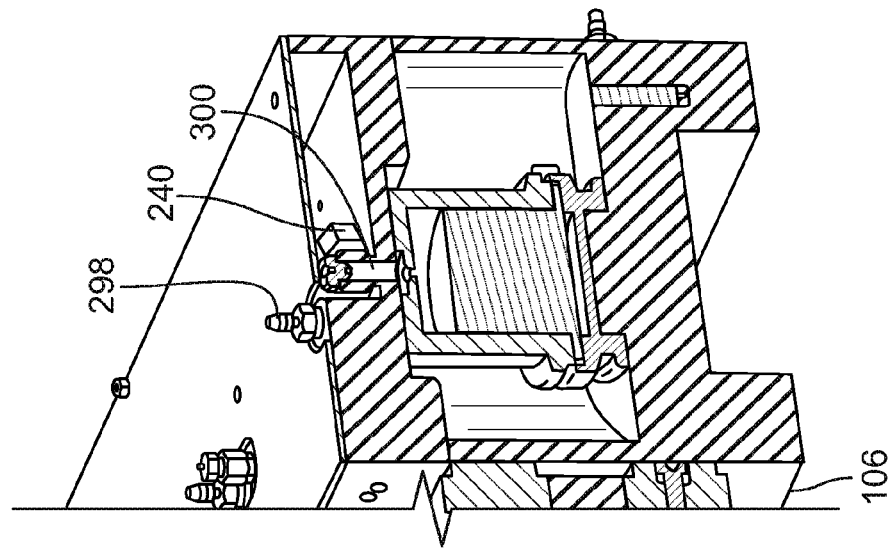
FIGS. 11A and 11B illustrate a cutaway view of the swatch block of FIG. 7 during a liquid challenge test.
Figure 11A:
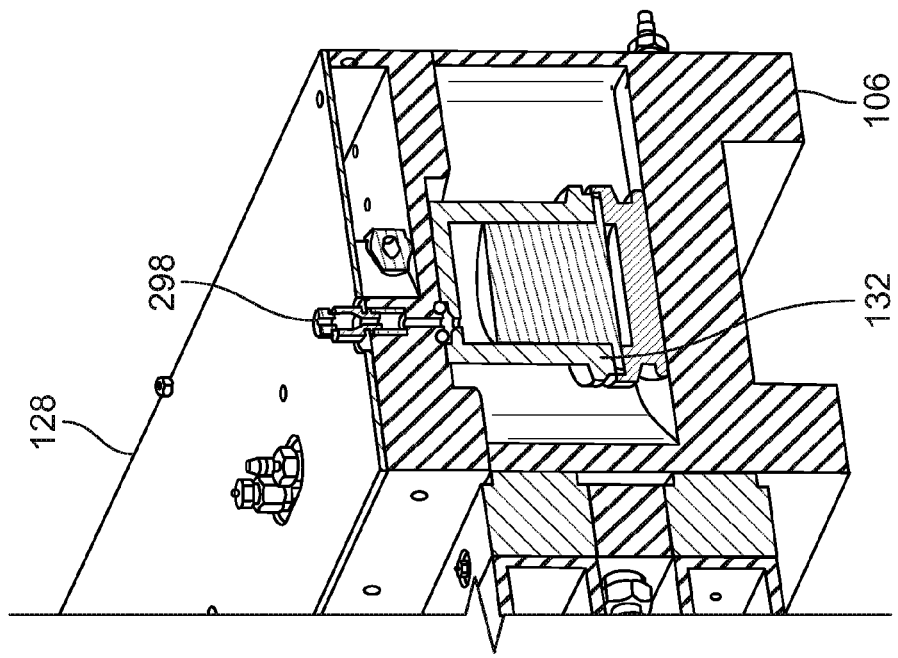

FIGS. 11A and 11B provide a cutaway view of swatch block 106 and lid 128 showing liquid challenge vent 298 and liquid challenge inlet 300. Inlet 300 is coupled to liquid challenge syringes 190 of FIG. 4 via Luer locks 194, tubing and connectors 240. Each syringe is connected to a different test cell. Vent 298 is provided to facilitate loading liquid into the test cells as would be understood by one of ordinary skill in the art.

Figure 12:
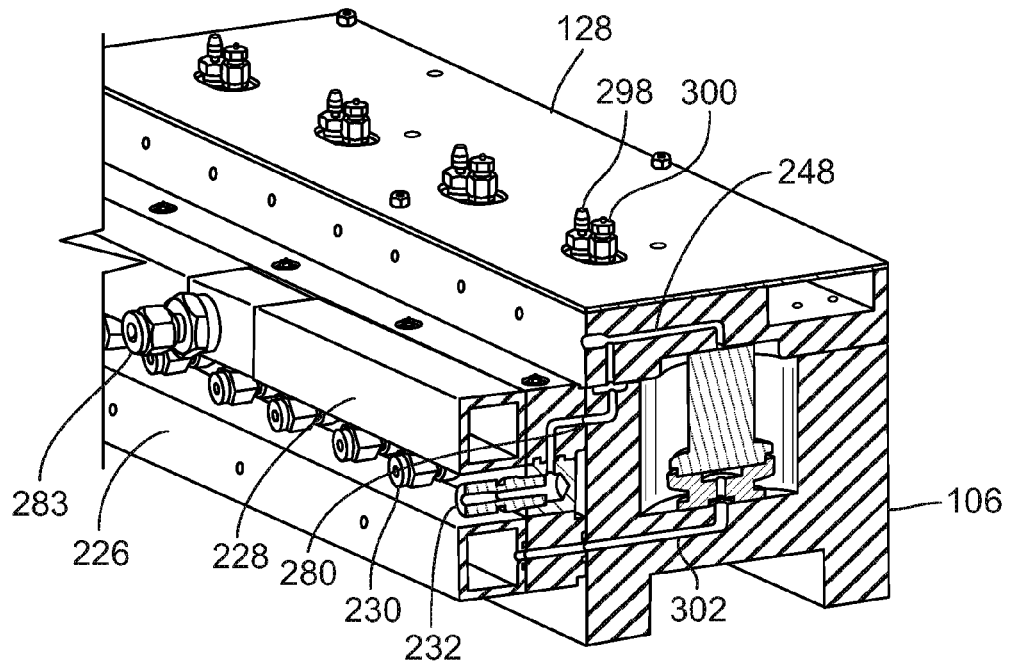
FIG. 12 illustrates a cutaway view of a swatch block of FIG. 7 during a vapor challenge test.

FIG. 12 is a cutaway view of swatch block 106 and lid 128 showing under swatch sweep inlet 302 and vapor challenge outlet 248. Under swatch sweep inlet 302 is coupled to air manifold 226 to provide a source of air to be drawn through the test cell when connecting both liquid and vapor challenge tests. Vapor challenge output 248 is connected to flow control manifold 206 through connection 232. This flow path provides an output for vapor that is circulated through a test cell during a vapor challenge.

Figure 13:
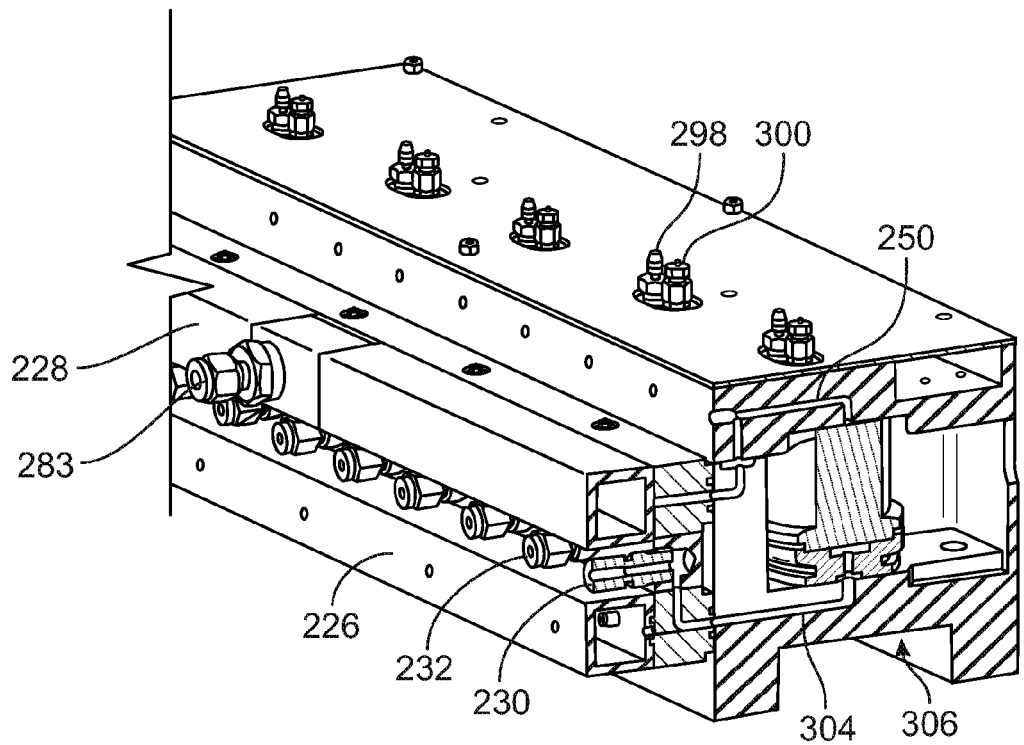
FIG. 13 illustrates a further cutaway view of a swatch block of FIG. 7 during a vapor challenge test.

FIG. 13 is a cutaway view of swatch block 106 and lid 128 showing under swatch sweep exit 304 and vapor challenge inlet 250. Under swatch sweep exit 304 is coupled to fitting 230 then to stream selection valve 204 of FIG. 5. As shown in FIG. 13, there is a fitting 230 and 232 for each cell. Fitting 230 for each cell is coupled to stream selection valve 204. For each test cell, stream selection valve 204 is also connected to flow control manifold 206. Cells that are not currently selected by stream selection valve 204 are still connected to manifold 206 so that air is continuously moving through the test cells.

Figure 14:
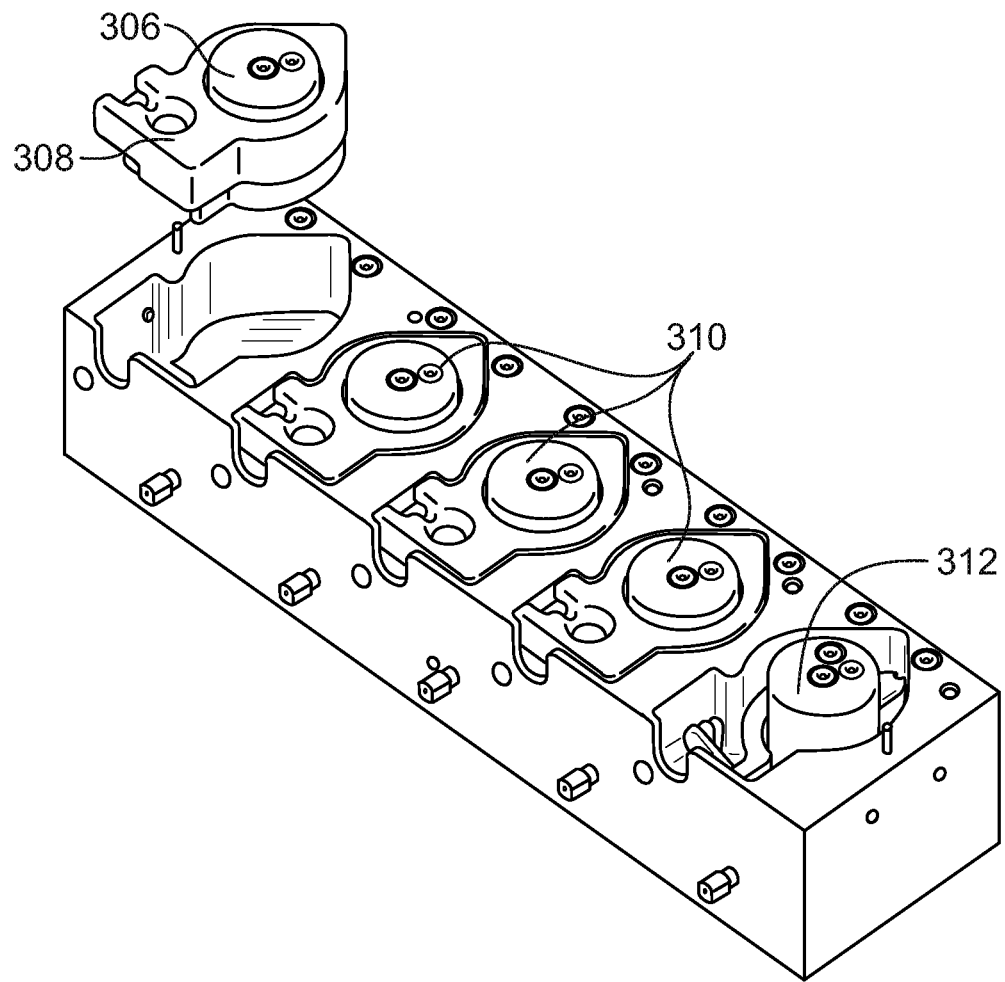
FIG. 14 illustrates how test cells are loaded into a swatch block.

FIG. 14 depicts swatch block 106 being loaded with a liquid challenge cell 306. Liquid challenge cells and vapor challenge cells are loaded in the same way. After the cell is placed in the swatch block, an aluminum spacer 308 is placed over the cell. Spacer 308 improves heat transfer into the challenge cell during warm-up. Three other liquid challenge cells 310 are loaded in swatch block 106. A blank cell is shown at 312. The use of a blank cell improves the analysis of test results but providing a control value. In a preferred embodiment, all cells positions will be loaded even if only one is being used. This helps keep lid 128 level during clamping by actuators 130 shown in FIG. 7. For a liquid challenge, syringes from the liquid challenge pump are connected to liquid challenge inlet 300 of FIG. 12 using tubing and fitting 240. For a vapor challenge, inlets 300 are not used. Vapor is generated using port 124 of FIG. 1. This pump is also used for calibration of the apparatus, as described below.

Operation and Software Control

The operation of permeation testing apparatus 100 will be described in conjunction with a description of the software used to control the apparatus. A computing device is coupled to apparatus 100 by means of LAN connection 108 of FIG. 1 as would be understood by one of ordinary skill in the art.

Figure 15:
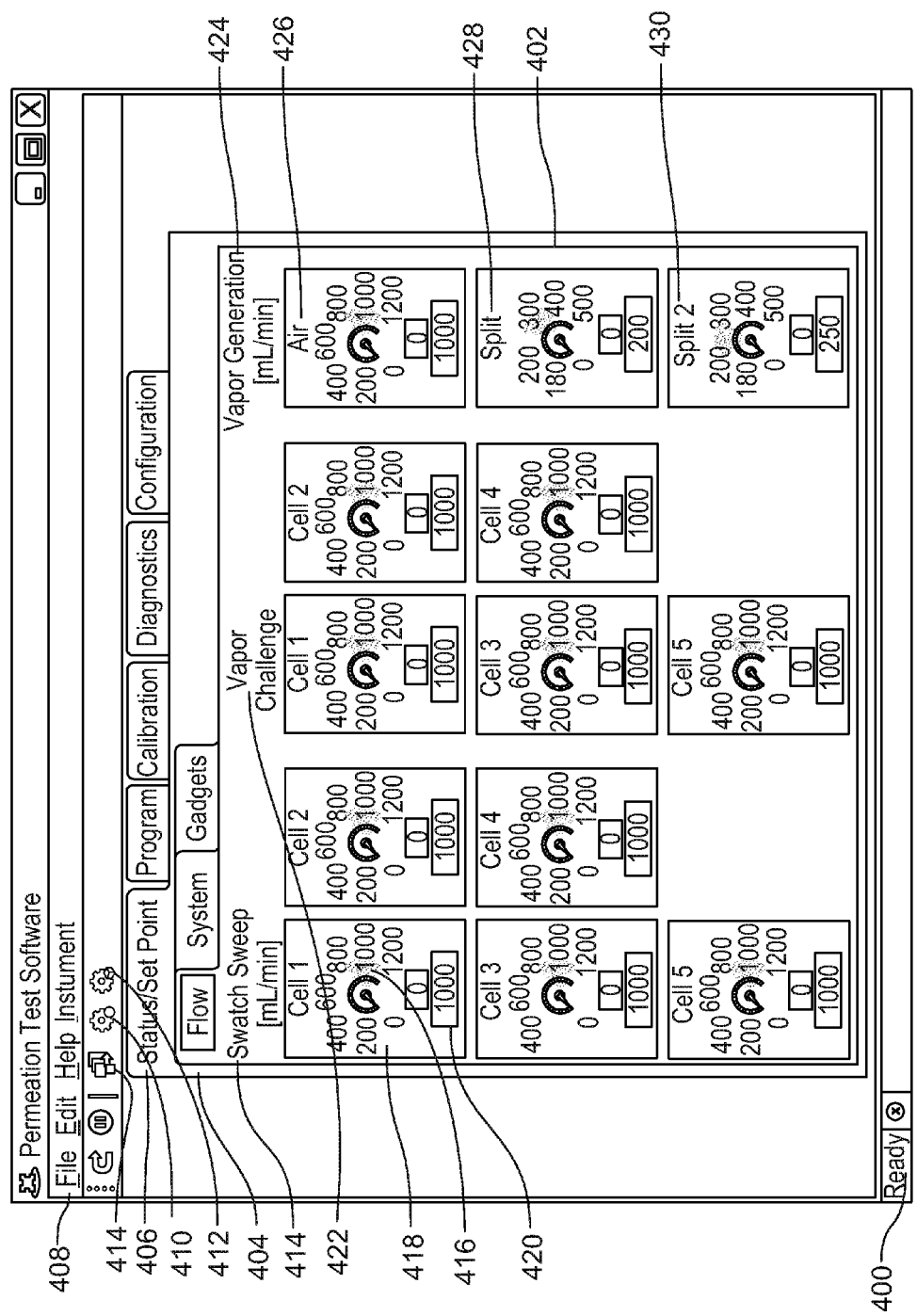
FIG. 15 depicts a main control screen for operating the permeation testing apparatus.

A main control screen is shown in FIG. 15. In all of the following diagrams, the exact arrangement of fields and windows is flexible as would be understood by one of ordinary skill in the art. In particular, FIG. 15 shows an initial view that opens when the software is first launched. A status field 400 in the lower left corner indicates whether or not communication with apparatus 100 has been established.

FIG. 15 depicts a plurality of gauges 402 which appear on the Flow tab in menu 404 under the Status/Set Point tab in menu 406. Gauges 402 indicate set point values for various elements in the testing device. When apparatus 100 is first turned on, it has no set point values. All values are defaulted to zero. This prevents the apparatus from initializing before the operator has downloaded the desired set points. When the software is first opened, the AC power relay and the oven fan automatically turn on. All of the other set points are still zero. The easiest way to enter the correct set points for a given test is to open a saved method. In a preferred embodiment, a new apparatus is delivered with a default method with set points that are appropriate for a first start up.

Menus 404, 406 and 408 of FIG. 15 provide a means for controlling the software. Referring to menu 408, the File menu that allows the operator to open an existing method, save a method and close the software. The Edit menu has two options: mark all and unmark all. For added convenience, these commands are provided as buttons as 410 and 412 respectively. 'Mark all' turns all of the set point fields that have numerical values yellow. This indicates that these fields are ready to be sent to apparatus 100. The 'unmark all' button removes the yellow highlight indicating that none of the values will be sent to apparatus 100. A send button is shown at 414. Clicking on the send button sequentially sends the set points to apparatus 100. As a set point is sent the value field for that device is un-marked. Once all of the fields are un-marked then the set points have been sent and will immediately take effect. This allows an operator to send the set points for a method before trying to start the method. In a preferred embodiment, oven 104 typically takes 30 minutes for all of the temperatures to be reached.

Under the Status/Set Point tab, three additional tabs are available as shown in menu 404. The Flow tab is shown in FIG. 15. This is the screen where most of the flows through apparatus 100 are set and monitored. The flow tab has three main sections: The swatch sweep section 414 is where the flow under the swatch is set and controlled. There is a set point and read back for each of the five cells. For following description, a single cell is referenced but all cell displays function similarly. A yellow highlight 416 on each dial 418 shows ±10% for each flow. As long as the needle stays within the yellow region 416, the analysis is in specification. Actual values are also displayed digitally in a field 420 located just below the dial.

Vapor challenge section 422 is where the flow of vapor over a swatch is set and monitored. Vapor is only available if the apparatus 100 hardware is configured correctly. There is a set point dial and read back field for each of the five cells.

The vapor generation section 424 controls the flows used to generate a calibration vapor. Like the vapor challenge section, this part of the system only functions when the hardware is configured correctly. Within vapor generation section 424, air control section 426 sets the flow rate for a dilution air stream used to generate a calibration vapor. The split 428 and Split 2 430 controls are used to control one of the two split valves located behind mixing tee 202 of FIG. 5 These are used to control the amount of sample being introduced into the dilution air stream.

Figure 16:
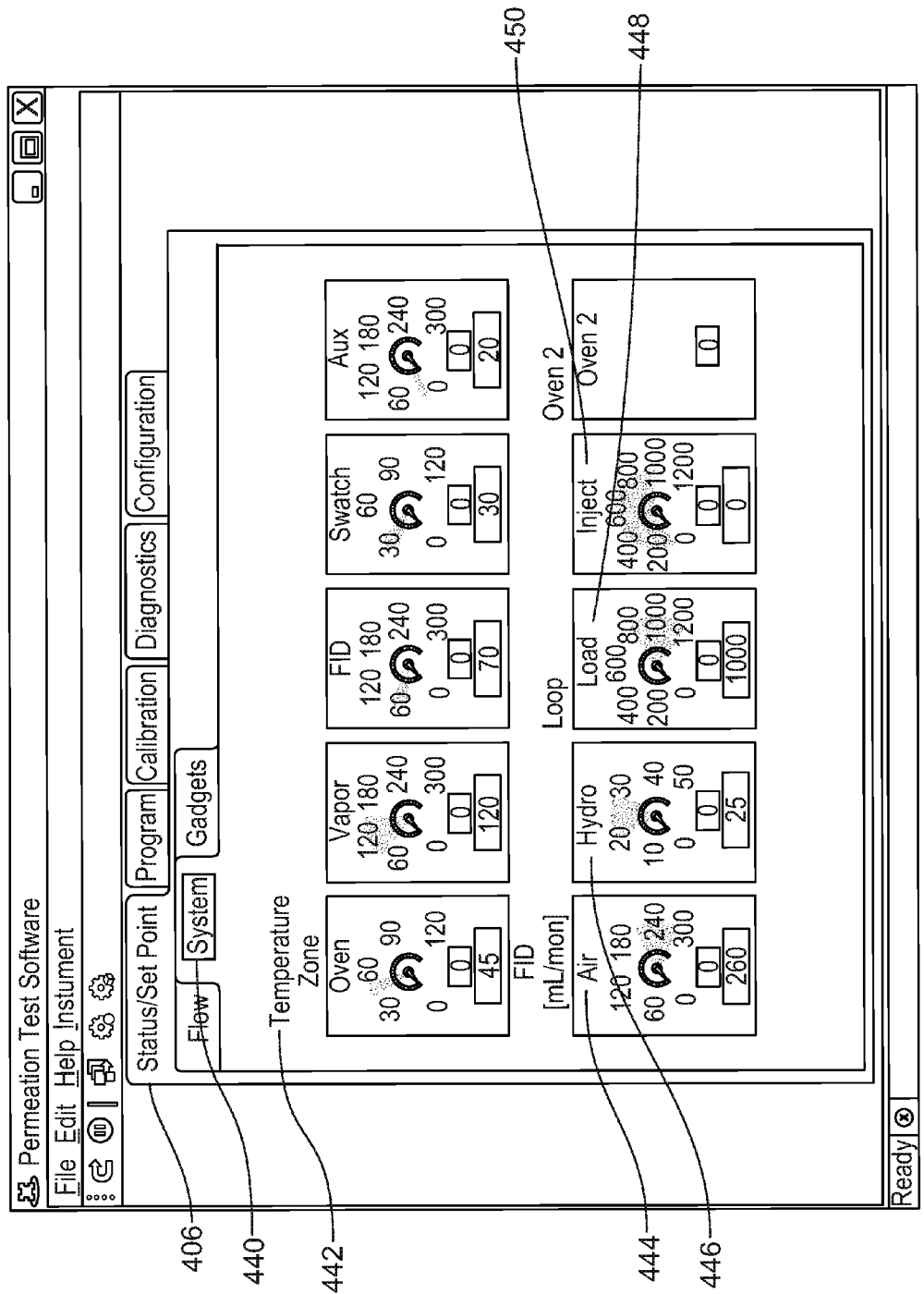
FIG. 16 depicts an additional control screen for operating the permeation testing apparatus.

Referring to FIG. 16, the System tab 440 under the Status/Set Point tab is shown. System tab 440 is used to control temperatures as well as gas flows for the FID 186 and the sample loopin injection valve 200.

Temperature zone 442 shows the various sections of apparatus 101 for which a temperature may be set, including oven 104 of FIG. 1, and heaters for vaporizer 182, FID 186 of FIG. 4, and swatch block 106 of FIG. 1. Swatch block 106 accommodates a strip heater underneath, as indicated 306 in FIG. 13. All the temperatures in this diagram are shown in degrees centigrade, although a Fahrenheit temperature scale could also be used as desired.

In a preferred embodiment, FID Air gauge 444 is set to 300 mL/minute and FID hydrogen 446 is set to 28 mL/minute. The loop load flow 448 is set to match the flow of the vapor generator air and the flows under the swatches. Using the flow switching valve allows the system to maintain flow through all of the control points. This flow maintains the sweep rate during sampling of a specific swatch of the calibration position. Inject flow 450 is typically set to 30 mL/minute. This is an air flow that sweeps the sample from the sample loop into the FID for detection.

Figure 17:
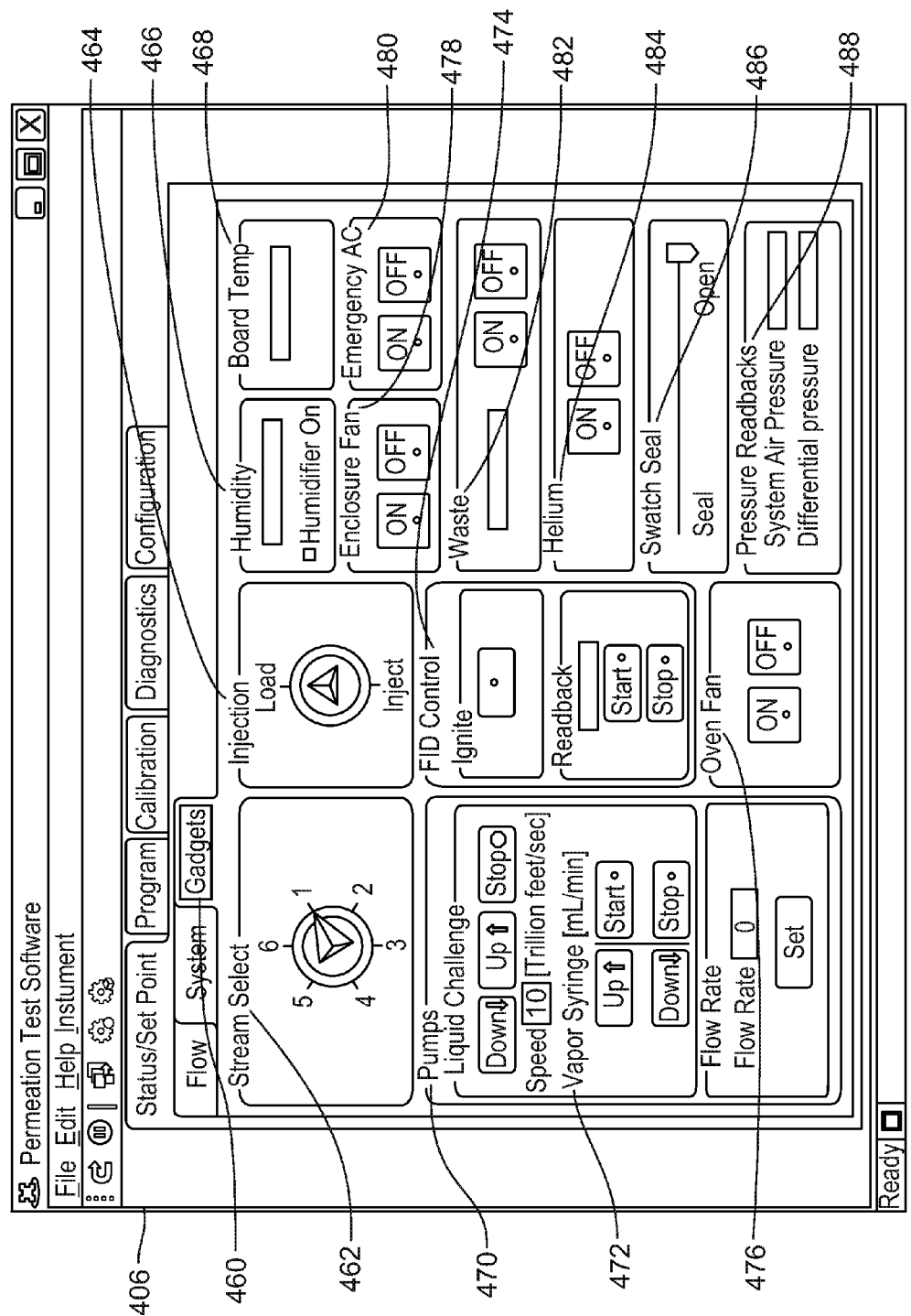
FIG. 17 depicts a further control screen for operating the permeation testing apparatus.

A third tab under the Status/Set Point tab is Gadgets tab 460 as shown in FIG. 17. This tab shows controls for the mechanical hardware of apparatus 100. In a preferred embodiment, many of these controls are for trouble shooting manual operation and are not available when apparatus 100 is being operated in an analytical run. Stream select section 462 controls the position of stream selection valve 204 of FIG. 5. The valve is moved by clicking on the number of the desired valve position. An arrow on the dial will rotate and point to the current position of valve 204. Injection control 464 functions the same as the stream select function and is used to move injection valve 202 of FIG. 5 from a load to an inject position. It is moved by clicking on the desired position. The arrow will point to the currently selected position.

Humidity field 466 displays the read back from a humidity sensor in apparatus 100. Board temp field 468 shows the temperature of the electronics motherboard. There are no controls associated with either of these fields.

Pumps section 470 is used to manually set and operate liquid challenge pump 122 and vapor challenge pump in gas port 124 of FIG. 1. Liquid challenge pump can be moved to the up position of the down position by clicking on the appropriate labeled arrow. Vapor syringe pump can be raised or lowered by clicking on the up and down arrows in vapor syringe section 472. An operator can also set a flow rate and manually start or stop the screw drive on the pump by clicking the start or stop buttons.

FID control section 474 is used for lighting FID 186 of FIG. 4. An operator can click the start button in the read back section. A signal from the FID is then displayed in the read back field. The operator can then click the ignite button to attempt to light the FID. The operator can tell if the FID is lit by looking at the signal in the read back section. When the FID is not lit, the read back will be near zero. When the FID is properly lit the read back signal is typically between 15,000 and 25,000. If the signal is lower than 15,000, the operator may need to temporarily set the hydrogen flow on the System tab of FIG. 16 to 35 mL/minute and try to relight the FID. Because of timing issues the FID read back is stopped automatically when the operator exits the gadgets screen. To see the signal upon return to the gadgets screen, the operator must click the start button in the read back section. After the FID is lit and has a signal between 15,000 and 25,000, the operator should decrease the hydrogen flow back to 28 mL/minute.

Figure 3B:
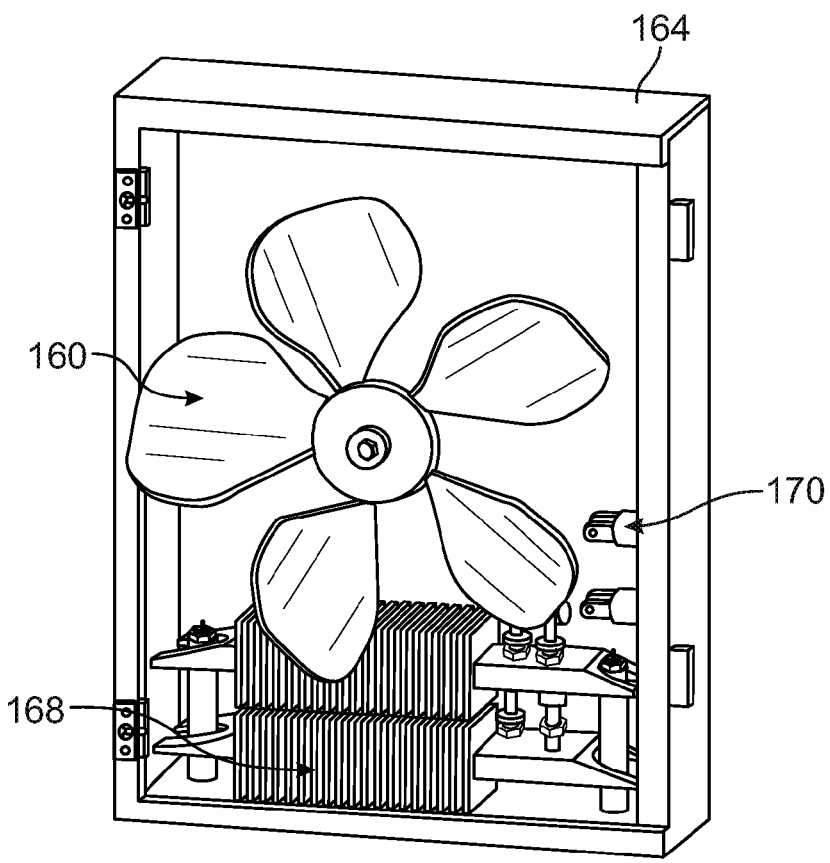

Oven fan section 476 is used to turn fan 160 on and off (FIGS. 3A and 3B). Turning the oven fan off also turns heater elements 168 off. Enclosure fan section 478 is used to turn the electronics cabinet cooling fan on and off. This fan should normally be left running at all times. This gadget can be used during servicing of apparatus 100 to stop air flow from the fan. Relay control 480 is used to turn on and off all of the AC powered parts of apparatus 100. The following items are run using AC power and will be turned off when the relay is turned off: oven heaters 168, internal oven fan 160, vaporizer heater, FID heater and the swatch heater. This relay is used for safety control of apparatus 100.

Waste section 482 provides controls for the Peltier waste trap. The trap can be turned on and off and the temperature of the trap can be monitored from this control.

Helium control section 484 turns the helium supply to the vaporizer on and off. The default for this control is on. Flow of helium should be maintained whenever the vaporizer is hot. This control is used to allow replacement of liners and septa in the vaporizer without having to turn off the entire apparatus 100. In a preferred embodiment, there is no restriction in the helium supply line. If there is a large leak in the vaporizer septum or other lines in the system the helium will be used at a high rate. This is necessary to ensure proper operation of the split flow controls.

Swatch seal control section 486 is used to seal swatch block 106 of FIG. 1 before a permeation test and to open the block after a test is completed. Sealing actuators 130 of FIG. 8 are moved by clicking on the open or close label. The arrow points to the current position. Pressure read backs are shown in section 488.

Figure 18:
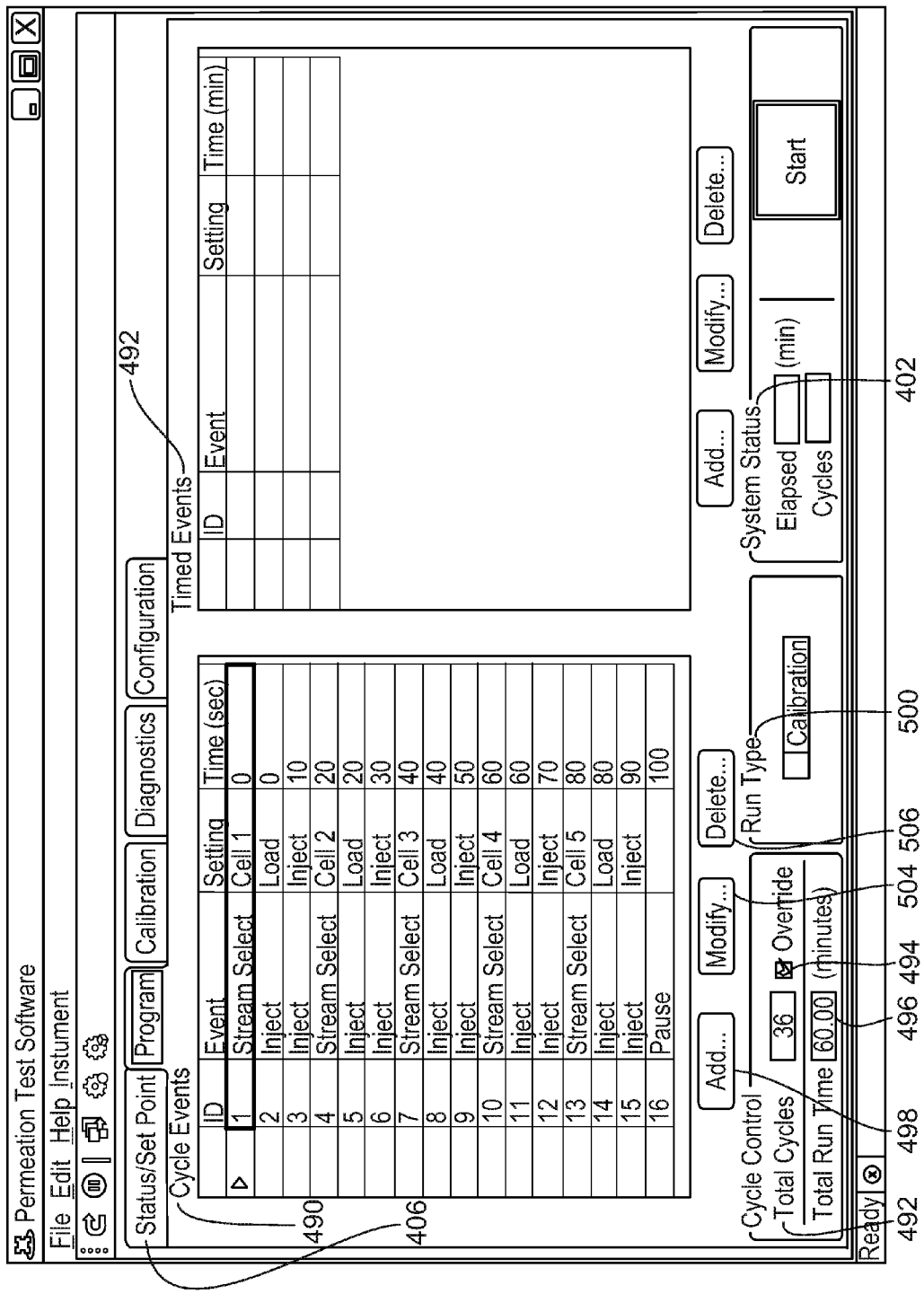
FIG. 18 depicts a cycle events table used for performing a liquid or vapor challenge test using the permeation testing apparatus.

The Program tab of menu 406 is shown in FIG. 18. This tab contains the controls that are used to set up an automated method. Apparatus 100 can be operated with cycle events or timed events. Cycle events appear in cycle events table 490. This table is used to control the sampling from each of the five test cells and a calibration channel. Placing cycle events in a table allows an operator to program one sequence of sampling for a given swatch test. A desired number of cycles are entered in field. To extend the test time, override button 494 is checked, the operator enters the run time for a method at 496 and the software calculates the number of cycles needed to reach the total time of the method.

Cycle Events

Figure 19A:
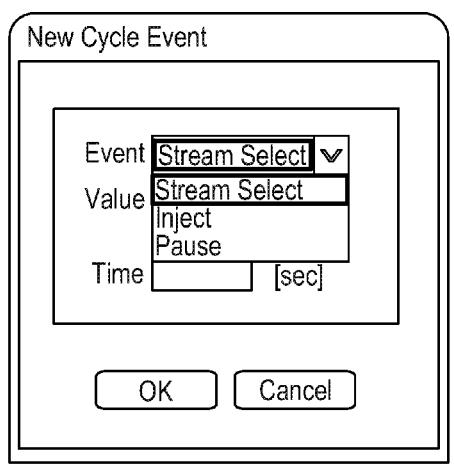
FIGS. 19A-19D depict menus used in programming challenge tests and calibration operations of the permeation testing apparatus.
Figure 19B:
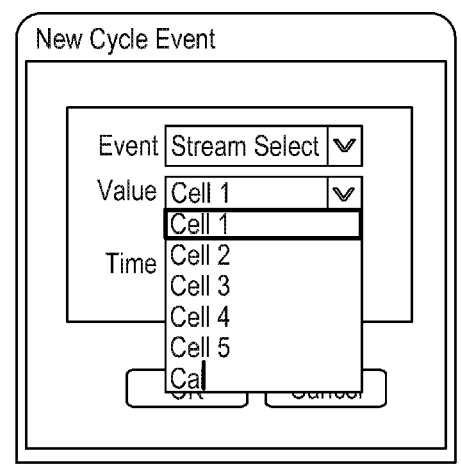
Figure 19C:
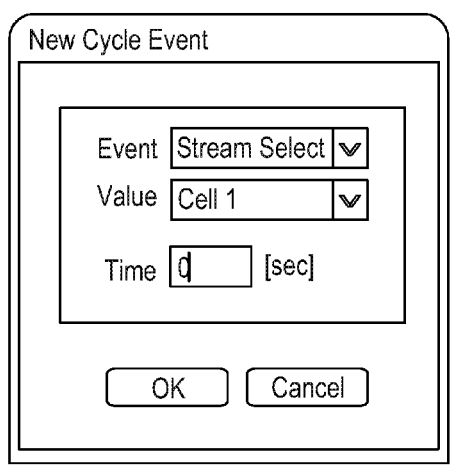
Figure 19D:
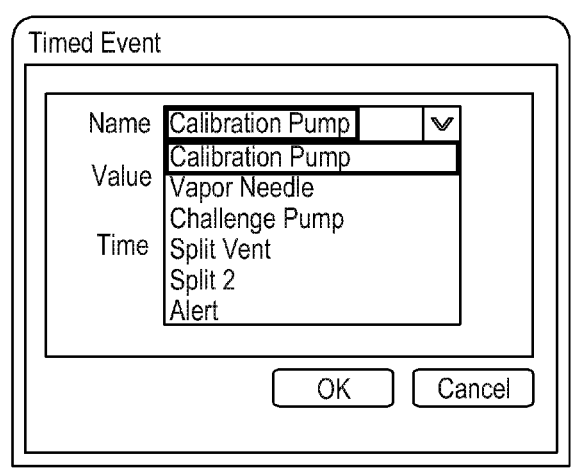

To create a Cycle Events Table as shown in FIG. 18, an operator first clicks Add button 498. This opens the dialog box of FIG. 19A showing three events that are controlled during a cycle. The first event is a Stream Select event which controls stream selection valve 204 of FIG. 5. When this event is selected, the options for the value field shown in FIG. 19B appear. These include any of the 5 cells or a calibration operation. Finally, a time value is entered as shown in FIG. 19C. This figure depicts an event where stream select valve 204 will move to cell position 1 at time zero. A second event shown in FIG. 19A is an Inject event. The options for an inject event include Inject and Load. The final event of FIG. 19A is a Pause event. This event allows time to pass while sample injection valve 200 and stream selection valve 204 are held in the last position. This is necessary to allow sample transition from one cell to the next.

Referring to FIG. 18, a method having 16 steps is shown in cycle events table 490. At step 1, the method moves the stream selection valve to position 1 and the injection valve to the load position at time zero. This allows the air flow from cell one to now through the sample loop. After the loop is swept for 10 seconds in step 2 the injection valve is moved to the inject position in step 3 and the stream from cell one is swept into the FID. The flow through configuration of the system means that flow is only stopped while the valves are actually moving. While the valves are in any position, the flow under the swatches is continuous.

After 20 seconds, at step 4 the stream select valve is moved to cell 2 and at step 5 the sample injection valve is moved back to the load position. The valves remain in this position until 30 seconds. This allows the sample stream from cell 2 to sweep the sample loop. At step 6 the sample from cell 2 is injected into the FID. Similar cycle events for cells 3-5 are shown in steps 7-15. A pause step at 16 is only needed at the end of the cycle time to allow completion of the final step in the cycle. At 40 seconds the method cycles back to step one and the process is repeated. The time for each step can be varied based on specific needs. In a preferred embodiment, the default configuration of apparatus 100 has a 6 mL sample loop. In the load positions the flows are normally configured to be 1000 mL/minute. This means that the sample loop is swept over 150 times during the 10 seconds that the loop is in the load position. The injection flow is set to 30 mL/minute. This means that most of the sample loop is swept into the FID during the inject step. Any material left in the loop at the end of the inject step is displaced by the next sample being loaded.

As explained above, in the cycle control area an operator can enter a number of cycles to complete in field 492. If the override option is checked, the operator enters a run time. In the example shown in FIG. 18, a run time of 65 minutes has been entered. Run type field 400 is used to select whether a run is going to be used for calibration or if the run is an actual swatch test. If the box is checked then that data that are output show the raw counts and a calibration report is generated. If the box is unchecked then the equations stored in the calibration tab and explained below are used to convert the counts into concentration and an analysis report is generated.

System status area 402 is where an operator starts a run and where the run time and number of cycles completed are displayed. Finally, Modify button 404 and Delete button 406 are used to enter events in a way that would be understood by one of ordinary skill in the art.

Timed Events

Figure 20:
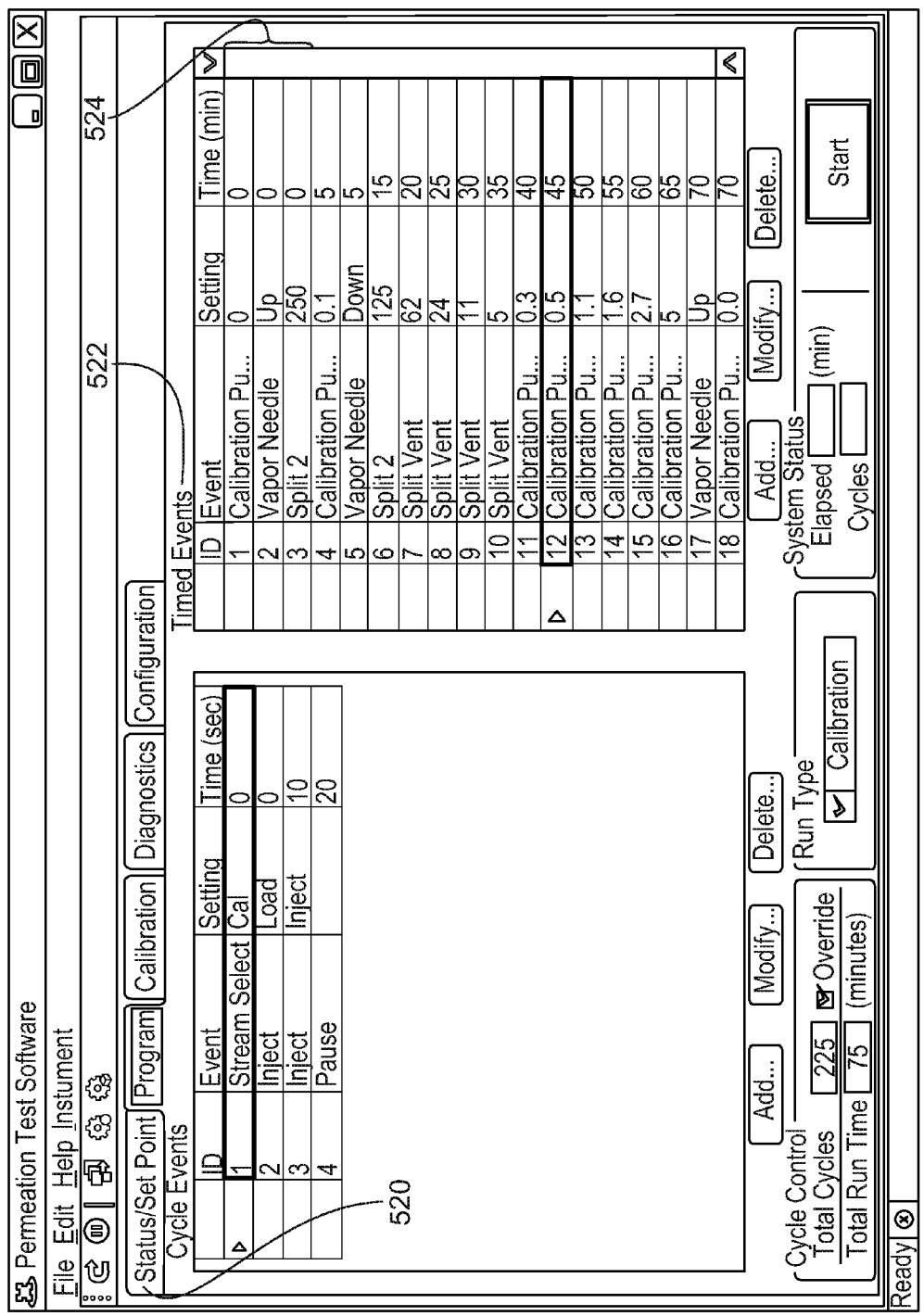
FIG. 20 depicts a cycle events table and timed event table used in a calibration operation.

Timed events table 522 of FIG. 20 differs from cycle events table 490 in one key way. The timed events are events that only occur once at a given time. To repeat an event the operator must enter the event a second time with a new time for the event to take place. Timed events are primarily used for calibration runs. A list of possible timed events is shown in FIG. 21D. The events include Calibration Pump, Vapor Needle, Challenge Pump, Split Vent, Split 2 and Alert.

Like the cycle events, each option has different possible values. If a Calibration Pump event is selected, the value is a numeric entry for the flow rate of the syringe in analytical carrier gas injection port 124 of FIG. 1. In a preferred embodiment, an entry of 5 would set the pump to deliver 5 μL/minute of flow to the vaporizer.

If a Vapor Needle event is selected, there are two options: up or down. This allows the operator to run a blank baseline then insert the syringe needle and deliver sample into the vaporizer. The operator can then move the syringe up at the end of a calibration to again establish a baseline.

For Challenge Pump there are two options: deliver or return. Deliver drives the pump down to push the liquid challenge out of the syringes and onto the swatches. Return pulls the plungers back to the top of the pump stroke.

For the Split Vent and Split 2 options the value is the flow rate in mL/minute from the first split vent. Split Vent has a flow range of 5-75 mL/minute. Split 2 has a flow range of 100 to 250 mL/minute.

For all of the options, an operator also enters a value in the Time field indicating how long the event should last.

Sample Calibration Program

FIG. 20 shows cycle events table 520 and timed event table 522 for a calibration run for acetone. Concentrations for various split and pump flow are calculated in a spreadsheet separately, then the flows are set to deliver the desired concentrations at each level.

The events start at 524 with the system running at a blank baseline for 5 minutes. At 5 minutes (steps 4-5), the syringe is lowered into the vaporizer and the syringe pump starts delivering acetone at 0.1 μL/minute. The flow rates of the pump and split flows with the calculated concentrations are shown in the table of FIG. 21. Calibration Points at steps 12-18 allow apparatus 100 to be tested at a variety of concentrations, determined by the speed with which a chemical is infused into vaporizer 182.

Method for Calculating Calibration Concentrations

To calculate the concentrations, the following information is needed:

Vaporizer Flow into dilution air stream (VF mL/minute)
Density of calibration fluid (ρ μ/μL) assume standard conditions
Split Flow (SF mL/min)
Calibration Pump Flow (PF μL/min)
Dilution Air Flow (AF mL/min)
First calculate the split ratio:

$$VF/(VF+SF)=SR \quad (1)$$

First calculate the split ratio:
where SR is the split ratio. Then calculate the flow from the syringe pump in μg/μL:

$$PF*\rho=MF \quad (2)$$

where MF is the mass flow of sample from the syringe pump. Then calculate the mass flow of sample into the dilution air stream.

$$MF*SR=MF_{AS} \quad (3)$$

where $MF_{AS}$ is the mass of sample flowing into the dilution air stream. Then calculate the concentration in the air stream:

$$MF_{AS}/AF=\text{total } \mu g/L \quad (4)$$

1 μg/L is equal to 0.1 μg/cm²/min because the system is using a 10 cm² swatch.

Method for Liquid Challenge Analysis of Swatches

Liquid and vapor challenges require specific hardware configurations as described above. Attempting to use a liquid challenge program with incorrect cells and plumbing will result in invalid data. Below is an example of cycle events and timed events used to analyze 5 swatch samples.

These would be entered in the software as discussed for FIG. 18. The override button would be checked and a run time set for 60 minutes. As discussed previously, the timed events have been set up for a 20 second cycle with a 10 second loop load time and a 10 second injection time. The timed events table has only one event: the delivery of the liquid challenge. It is done at 5 minutes to allow for the determination of the system blank baseline. The program cycles through the cells because only one cell can be tested at a time.

Event: Stream Select, Setting: Cell 1, Time: 0
Event: Inject, Setting: Load, Time: 0
Event: Inject, Setting: Inject, Time: 10
Event: Stream Select, Setting: Cell 2, Time: 20
Event: Inject, Setting: Load, Time: 20
Event: Inject, Setting: Inject, Time: 30
Event: Stream Select, Setting: Cell 3, Time: 40
Event: Inject, Setting: Load, Time: 40
Event: Inject, Setting: Inject, Time: 50
Event: Stream Select, Setting: Cell 4, Time: 60
Event: Inject, Setting: Load, Time: 60
Event: Inject, Setting: Inject, Time: 70
Event: Stream Select, Setting: Cell 5, Time: 80
Event: Inject, Setting: Load, Time: 80
Event: Inject, Setting: Inject, Time: 90
Event: Pause, Setting: <blank>, Time: 100

Method for Vapor Challenge Analysis of Swatches

The cycle events for a vapor challenge are the same as those for a liquid challenge as described above. The timed events are as follows:

Event: Split Vent, Setting: 5, Time: 0
Event: Vapor Needle, Setting: Up, Time: 0
Event: Calibration Pump, Setting: 1, Time: 5 min
Event: Vapor Needle, Setting: Down, Time: 5 min Like the liquid challenge, the cycle events are configures to test 5 cells on a 20 second cycle time. The vapor challenge is started after 5 minutes to allow for system baseline determination. Using the calculations described above the challenge vapor concentration for acetone would be 225.7 μg/L.

Numerous alternative implementations of the present invention exist. For example, it is possible to provide a special test cell with an onboard pressure transducer as a means of characterizing the pressure differential of the system. In addition, one of ordinary skill in the art would understand that specific arrangements and sizes of components described above could be changed as needed while still accomplishing the described functions.

The apparatus 100 in one example comprises a plurality of components such as one or more of electronic components, hardware components, and computer software components. A number of such components can be combined or divided in the apparatus 100. An example component of the apparatus 100 employs and/or comprises a set and/or series of computer instructions written in or implemented with any of a number of programming languages, as will be appreciated by those skilled in the art.

The steps or operations described herein are just for example. There may be many variations to these steps or operations without departing from the spirit of the invention. For instance, the steps may be performed in a differing order, or steps may be added, deleted, or modified.

Although example implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus for testing the chemical permeation of materials, comprising:
   a swatch block having an air distribution manifold, a chemical vapor challenge manifold, and a heater block having a plurality of openings, each of said openings for receiving a test cell for holding a swatch of material to be tested between a top half and a bottom half of each test cell;
   a lid and a clamping means for securing said lid to said swatch block after said test cells are inserted in said plurality of heater block openings;
   a first flow path for passing a chemical under test through the top half of each cell;
   a second flow path for extracting vapor from the bottom half of each cell;
   a detector for receiving vapor from the second flow path and analyzing it for presence of the chemical under test; and
   a vacuum for maintaining an air flow through the test cells and the first and second flow paths.

2. The apparatus of claim 1, wherein the chemical under test is provided to said test cells in a liquid form.

3. The apparatus of claim 2, wherein the chemical under test is provided in a separate syringe for each test cell and the first flow path further comprises:
   tubing coupling each syringe individually to each test cell; and
   a liquid challenge pump for expelling the chemical under test from the syringe into the tubing.

4. The apparatus of claim 1, wherein the chemical under test is provided to said test cells in a vapor form.

5. The apparatus of claim 4, wherein the chemical under test is provided in liquid form in a syringe and the first flow path further comprises:
   a vaporizer for receiving the liquid chemical under test from the syringe and vaporizing the liquid chemical; and
   said vapor challenge manifold receiving the vaporized chemical under test and distributing the vaporized chemical to the plurality of test cells.

6. The apparatus of claim 1, further comprising one or more heaters for maintaining temperatures in the apparatus.

7. The apparatus of claim 6, further comprising a computer for electrically controlling the heaters and the first and second flow paths.

8. A method of testing the chemical permeation of materials, comprising the steps of:
   loading a swatch of material to be tested between a top half and a bottom half of each of a plurality of test cells;
   inserting the plurality of test cells in a swatch block having an air distribution manifold, a chemical vapor challenge manifold, and a heater block having a plurality of openings, each of said openings for receiving an individual test cell holding a swatch of material to be tested between a top half and a bottom half of each test cell;
   securing a lid to said swatch block after said test cells are inserted in said plurality of heater block openings;
   initiating a first flow of a chemical under test through the top half of each cell;
   initiating a second flow of vapor extracted from the bottom half of each cell; and
   analyzing the vapor from the bottom of each cell for presence of the chemical under test.

9. The method of claim 8, wherein the chemical under test is provided to said test cells in a liquid form.

10. The method of claim 9, wherein the chemical under test is provided in liquid form in a separate syringe for each test cell and the step of initiating a first flow further comprises:
    providing tubing coupling each syringe individually to each test cell; and
    initiating a liquid challenge pump to expel the chemical under test from the syringe into the tubing.

11. The method of claim 8, wherein the chemical under test is provided to said test cells in a vapor form.

12. The method of claim 11, wherein the chemical under test is provided in liquid form in a syringe and the step of initiating a first flow further comprises:
    expelling the liquid chemical under test from the syringe into a vaporizer;
    vaporizing the chemical under test from the syringe; and
    sending the vaporized chemical to a vapor challenge air manifold which distributes it to the plurality of test cells.

13. The method of claim 8, further comprising the step of controlling one or more heaters to maintain temperatures in the apparatus.

14. The method of claim 13, further comprising the step of using a computer to electrically control the heaters and the first and second flow paths.

15. The method of claim 8, wherein said first and second flows are maintained through use of a vacuum.

* * * * *